United States Patent [19]

Weyant

[11] Patent Number: 4,513,752
[45] Date of Patent: Apr. 30, 1985

[54] BIPOLAR SENSING SYSTEM

[75] Inventor: Robert R. Weyant, Claremont, Calif.

[73] Assignee: Pacesetter Systems, Inc., Sylmar, Calif.

[21] Appl. No.: 458,248

[22] Filed: Jan. 17, 1983

[51] Int. Cl.[3] .............................................. A61B 5/04
[52] U.S. Cl. ............................. 128/696; 128/419 PG; 330/149
[58] Field of Search ................ 128/419 PG, 695–696, 128/702–704, 706, 708, 710, 901; 330/261, 149; 307/350, 358

[56] References Cited

U.S. PATENT DOCUMENTS

| 4,152,659 | 5/1979 | Gordon | 330/149 |
| 4,184,487 | 1/1983 | Peyer | 128/710 |
| 4,379,459 | 4/1983 | Stein | 128/419 PG |

OTHER PUBLICATIONS

Kenedy et al., "Electrocardiograph R–Wave Detector" *IBM Technical Disclosure Bulletin*, vol. 19, No. 3, Aug. 1976, pp. 763–764.

Duffin, Jr. et al., "A 24–Channel Electrocardiographic PreAmplifier" *Proc. 23rd ACEMB*, Nov. 15-19, 1970, p. 193.

Plumb et al., "A Noise Suppressor for Neurophysiological Recording of Impulse Activity" *IEEE Trans. Bio–Med. Eng.*, Oct. 1964, vol. 11, No. 4, pp. 157–159.

*Primary Examiner*—William E. Kamm
*Assistant Examiner*—Mitchell J. Shein
*Attorney, Agent, or Firm*—Robert R. Meads; Bryant R. Gold

[57] ABSTRACT

The present invention is a sensing amplifier circuit for a tissue stimulator (72) for supplying or attenuating far field signal voltage artifacts comprising a full differential amplifier having a first (94, 136) and second (96, 142) stage amplifiers for respectively receiving a second and first signal voltage output from a sensing mean (80, 82), and a switch means for controlling an input of the second signal voltage output from said sensing means to the first stage amplifier (94, 136).

9 Claims, 3 Drawing Figures

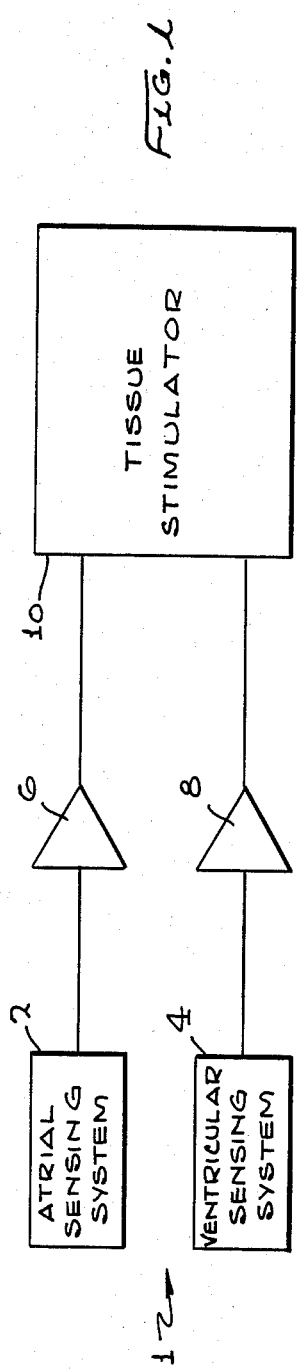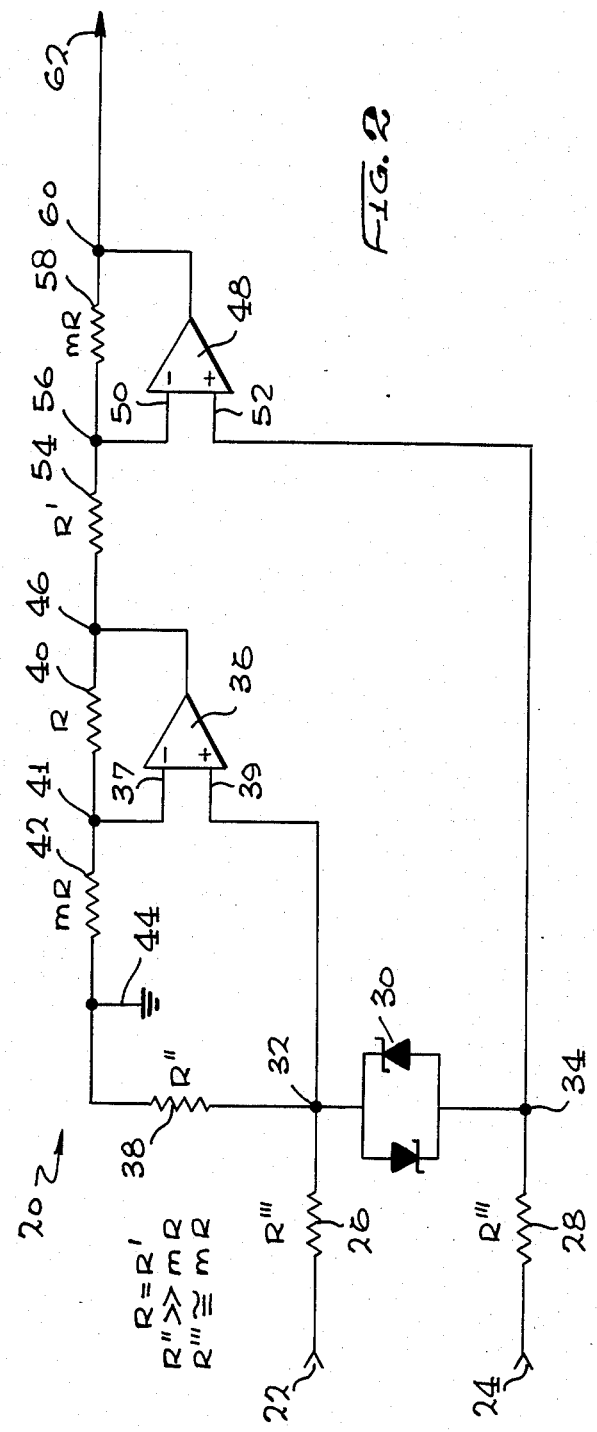

BIPOLAR SENSING SYSTEM

TECHNICAL FIELD

The technical field of the present invention is the field of circuits used for signal voltage amplification for voltages sensed by a sensing system for input into the logic circuitry of a tissue stimulator.

BACKGROUND ART

In the past, one of the problems with sensing systems for tissue stimulators was the inability of the system to attenuate far field voltage artifacts. These artifacts were created by depolarization of body tissue in areas remote from the tissue the sensing system was adjacent. These artifacts were manifested as voltage potentials carried into a particular area of tissue to which the sensing system was adjacent. The sensing system would detect (sense) these voltages and interpreted them as depolarization events taking place in the local tissue when such depolarizations were above the threshold sensing voltage of the system. These far field signal voltages which surpassed the threshold voltage were input into the sensing section of the tissue stimulator. Such input signals could cause activation of certain pacing schemes for the stimulator.

The tissue stimulator which is of primary concern is a cardiac pacemaker. The lead systems associated with a cardiac pacemaker are either unipolar or bipolar. These lead systems fulfill two functions. The first function is to provide an electrical conduit by which an output pulse is delivered to stimulate the tissue to which the tip of the lead is adjacent. The second function is that it provides the sensing system to sense electrical activity as it takes place near the distal end of the lead system. The lead systems can be disposed in the atrium alone, ventricle alone, or both the atrium and ventricle. In present day lead systems, the atrial lead system usually comprises an atrial J-lead, while the ventricle lead system is a traditional straight lead.

In the past, whether there was a unipolar or bipolar lead system, there was a need for a sensing amplifier to amplify the sensed signal voltages before they were input into the sensing section of the tissue stimulator. In most cases the signal voltages would have voltage potentials in the millivolt range and amplification was mandatory. The signals which were amplified and input into the sensing circuit of the tissue stimulator indicated that there was a sensed signal voltage received by the unipolar or bipolar lead system. In most cases, only signal voltages sensed due to the depolarization of a tissue in close proximity of the sensing lead would produce a voltage great enough to overcome the threshold limitation of the amplifier circuit. These events would be either natural depolarizations of the tissue, depolarizations caused by an output pulse generated from the tissue stimulator, or the signal voltages produced by far field artifacts which were transmitted through tissue or body fluid to the tissue near the distal end of the lead system.

However, it was not desirable for the tissue stimulator to acknowledge and be responsive to such far field artifacts. The most desirous situation was to have a stimulator that would be responsive only to sensed depolarizations caused by natural P-waves or R-waves; or atrial or ventricular pulses output by the cardiac pacemaker in the tissue near the distal end of the lead system. If this was not the case and the tissue stimulator was responsive to far field artifacts viewing them as local depolarization of tissue, it could effect the pacing scheme of the tissue stimulator.

In order to alleviate the problem of sensing far field artifacts, present day tissue stimulators have blocking or blanking periods instituted in their programming to block atrial sensing after there is an atrial pulse or a sensed P-wave. This blanking period is generally long enough so that, if there is caused a retrograde signal transmitted back to the tissue near the distal end of the lead system it will not be sensed by the sensing system. Additionally, in situations where the tissue is that of the ventricle, and it is not desirable to sense the atrial depolarizations in the ventricle, there are blanking periods in ventricle sensing systems to prevent the sensing of such activity.

When the tissue stimulator is a cardiac pacemaker, there are situations in which there is a desire (or need) for it to remain uncommitted during the atrial/ventricle transmission time (AV delay). This AV delay is the normal time in which the atrial sensing system is blanked or blocked. In order to successfully carry this out, there must be a method by which to reject the retrograde transmission of the ventricular response to the atrial depolarization. The type of pacers in which this problem can arise are generally pacers that are triggered by an atrial depolarization. Therefore, pacers such as those pacing in modes AAI, AAT, VAT, and DDT will be activated by sensed far field signal voltages caused by the ventricular response to an atrial depolarization.

There have been studies of sensing systems comprising unipolar or bipolar lead systems. In an article by Parsonnet, Myers and Kresh, *Characteristic of Intercardiac Electrograms II: Atrial Endocardio Electrograms,* Vol. b3, July–Aug. 1980, pp. 406–417, the authors addressed investigations made relating to sensing systems which were unipolar and bipolar. In the article, the results of the testing revealed that problems were found regarding sensing of far field artifacts. In the article the authors produced a number of tables and graphs showing the representations of their findings. They did find that there was some attenuation of far field effects when a bipolar sensing system was used. However, there was no indication that they could control the amount of far field effects which were sensed by the sensing system. It was basically hit or miss whether there was sensing of the artifacts.

In their investigations, the authors used a standard sensing system, (with either bipolar or unipolar sensing systems) with standard sensing amplifiers for giving a certain amount of voltage gain to the sense signals. Their system was result oriented, not circuit oriented, and did not particularly take into account the characteristics of local depolarization wave fronts and far field artifact wave fronts. No apparatus at present has endeavored to use these characteristics to configure a circuit to attentuate far field artifacts. The present invention overcomes these problems noted in the foregoing.

DISCLOSURE OF INVENTION

The present invention is a sensing amplifier circuit for a tissue stimulator for supplying or attenuating far field signal voltage artifacts. When the tissue stimulator is a cardiac pacemaker, the amplifier circuit of the invention receives sensed signal voltages from local depolarizations and far field artifacts and supplies them to the sensing section circuit of the stimulator The sensing amplifier circuit of the invention replaces the standard sensing amplifier connected between the stimulator and the sensing system.

The sensing amplifier circuit of the invention receives discrete signal voltages representing depolarizations of tissue and attenuates these signal voltages received based on their characteristics. The present invention is a full differential amplifier sensing circuit which has the ability to be switched to provide signal voltages to the first or second stage. When both stages are used, there will be sensing of the far field artifacts, but there is attenuation of the signal voltage at the output side of the circuit.

The present invention in its primary embodiment comprises a full differential amplifier having a first and second stage from receiving a first and a second signal voltage output from a sensing means, respectively. When a bipolar lead system is used the first stage is connected to the ring electrode and the second stage is connected to the tip electrode. The circuit has a switch means for controlling the input of a second signal voltage to the first stage. When the switch is opened, the second stage amplifier receives a first signal voltage from the lead sensing system and the first stage amplifier is grounded to the case ground. In this configuration, the second stage amplifier output is indicative of local signal voltages or far field signal voltage artifacts sensed by the tip electrode or sensing means. This open switch configuration is used when there is a unipolar lead system used or when a bipolar system is used and it is desired to use it in a unipolar sensing configuration.

When the switch is closed, the first stage amplifier receives the second signal voltage sensed by the ring electrode of the lead sensing system and the second stage amplifier receives the first signal voltage sensed by the tip electrode of the lead sensing system. In this configuration, the output of the first stage amplifier is tied to the input of the second stage amplifier and the second stage amplifier output is substantial for local depolarization signal voltages and attenuated for far field signal voltage artifacts.

In order to carry out the grounding of the first stage amplifier, a shunt resistor is connected across the input terminals to the first stage operational amplifier. When the switch is open, the positive input terminal to the first stage operational amplifier is grounded through the shunt resistor.

An object of the invention is to provide a sensing amplifier circuit which will supply or attenuate a far field signal voltage artifacts sensed by a sensing means associated with a tissue stimulator.

Another object of the invention is to provide a sensing amplifier circuit which in one mode of operation allows for the attenuation of far field signal voltage artifacts sensed by the sensing means and in a second mode to allow amplification of such artifacts sensed by the sensing means.

A still further object of the invention is to provide a sensing amplifier circuit for a tissue stimulator which does not require the use of programmed blanking periods within the sensing system to prevent far field effects for effecting the pacing scheme of the tissue stimulator.

These and other objects of the invention will be described in detail in the subsequent paragraphs.

BRIEF DESCRIPTION OF DRAWINGS

FIG. 1 shows the sensing amplifier disposition for the standard tissue stimulator.

FIG. 2 shows the basic embodiment of the sensing amplifier circuit of the invention.

BEST MODE FOR CARRYING OUT THE INVENTION

Figure 3:
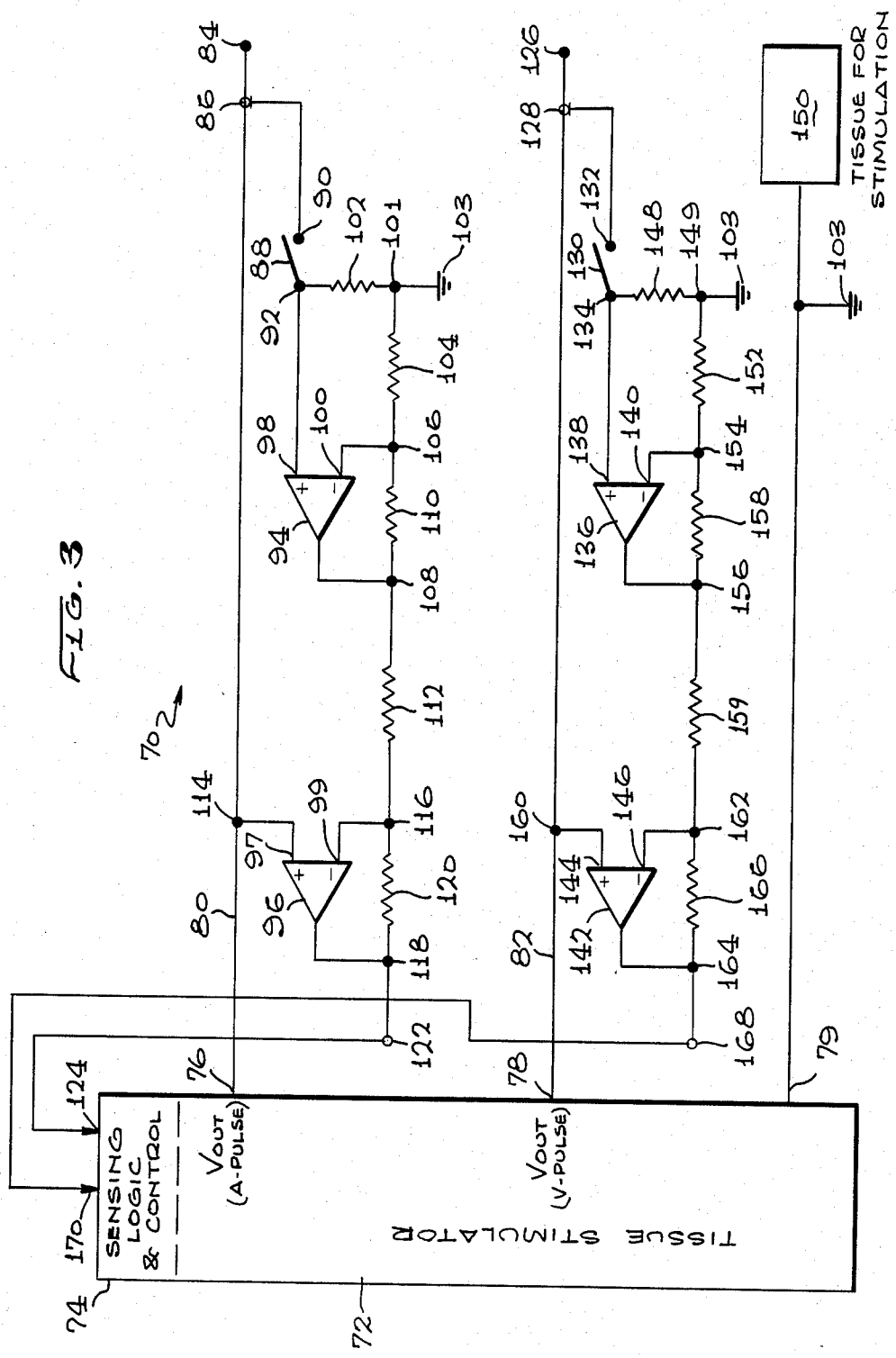
FIG. 3 shows the sensing amplifier circuit of the present invention configured for use with a tissue stimulator.

The present invention is a sensing amplifier circuit for a tissue stimulator for supplying or attenuating far field signal voltage artifacts.

Referring to FIG. 1, generally at 1, the conventional configuration between sensing systems, sensing amplifiers and a tissue stimulator is shown for a bifocal system. The atrial and ventricular sensing systems 2 and 4, respectively, are either a bipolar or unipolar lead system. Sensing systems 2 and 4 supply sensed signal voltages to sensing amplifier 6 and 8, respectively. The sensing amplifiers 6 and 8, then supply the respective amplified sensed signal voltages to tissue stimulator 10. The tissue stimulator 10 acts upon these amplified signal voltages for the proper pacing scheme of the tissue stimulator.

Sensing amplifiers 6 and 8 are usually configured to consist of an amplifier section and filter section. The amplifier section usually consists of a single operational amplifier. There are other more complicated systems which utilize filter sections and various other circuit components, but the basic system is as shown in FIG. 1.

Sensing amplifiers 6 and 8 have voltage thresholds, below which, they will not amplify the received signal. The filter section of the amplifiers is intended to exclude unwanted portions of the signal voltage received by the amplifiers and produce a clean amplified signal for input into the sensing logic of the tissue stimulator 10.

The sensing amplifiers 6 and 8, as long as a threshold voltage was met, will indiscriminately amplify the received signal voltage whether or not it was wanted or unwanted. There is extreme difficulty in providing filtering means which could properly filter the unwanted signals without the added problem of filtering wanted signal voltages sensed. Sensing amplifier 6 and 8, as shown in FIG. 1, did not have the ability to distinguish and attenuate, at will, the far field artifacts which have different characteristics than signal voltages created by local tissue depolarization in the proximity of the sensing system.

It has been noted in the article by Parsonnet, Myers, and Kresh, *Characteristics of Intercardiac Electragrams II: Atrial Endocardio Electrograms,* Pace Vol. III: 406-17, July-Aug. 1980, that bipolar leads cause some attenuation of the far field artifacts sensed by the sensing systems (lead systems). This attenuation was based on the placement of the tip and ring electrodes with respect to the depolarization wave front. The attenuation was not based on the ability of the sensing amplifier 6 or 8 attenuating the far field artifacts because of their characteristics. This attenuation was primarily based on the placement of the lead electrodes (tip and ring) and whether they were normal or parallel to the depolarization path of the wave front in the tissue.

Referring to FIG. 2, the basic sensing amplifier circuit of the invention is shown generally at 20. This circuit is connectable to a bipolar or unipolar lead system. When a bipolar lead system is used, the signal voltages sensed by the tip electrode is input at 24 and the signal voltages sensed by the ring electrode input at 22 of the circuit. The circuit is two-stage differential amplifier. In the first stage, which receives the signal voltage sensed at the ring electrode, the sensed signal voltage travels through resistance means 26, which acts as the input impedance, to a common connection point 32. This signal voltage from 32 is input to positive input terminal 39 of first stage operational amplifier 36. Operational amplifier 36 is of a conventional type commonly used in many electronic circuits. The negative input of the first stage amplifier is connected to a case ground 44 through resistance means 42.

When a signal voltage is applied to the positive terminal of amplifier 36, it provides an output because of the voltage difference between the positive and negative input terminals. The amplifier will attempt to equalize the positive and negative inputs through the feedback network of the amplifier 36. The output signal voltage of operational amplifier 36 is supplied to common connection point 46 of the circuit. Common connection point 46 supplies the output signal voltage to the feedback network of amplifier 36. The feedback networks acts as a voltage divider and holds the negative input terminal at a voltage equal to the signal voltage input at 39, by adjustment of the signal voltage output of amplifier 36. Because of the resistance ratios of resistors 40 and 42 a majority of the voltage drop of the line is across resistor 42, therefore, the voltage output of 36 is only slightly higher than that input to the positive input terminal 39.

The common connection point 46 also supplies the output of first stage amplifier 36 to the negative input terminal of second stage amplifier 48. The output of the first stage amplifier 36 is supplied to the negative input terminal of amplifier 48 after passing through resistance means 54. This second stage comprises amplifier 48 having a feedback network with resistor 58 contained therein. The second stage input resistor 54 has a small value compared to the value of feedback network resistor 58. The positive input terminal 52 of operational amplifier 48 receives the signal voltage sensed by the tip electrode of the sensing system after it passes through resistance means 28, which has the same resistance value as resistance means 26 and acts as the input impedence for the second stage.

In the ideal situation, when the two signals are supplied to operational amplifier 48 via positive terminal 52 and negative terminal 50, they will be matched. Therefore, no output will be supplied by operational amplifier 48 to common connection point 60. However, this ideal condition never exists, there will be some difference in the input voltage value and an output from amplifier 48. When there is an output from amplifier 48 it is supplied to connection point 60 which is connected to common connection point 56 via the feedback network. Point 56 is the virtual zero voltage point of the circuit. The feedback network therefore is used to isolate the input signal voltage to negative input terminal 50 and through its combined activity with the feedback network will match the input to the positive input terminal 52. The common connection point 60 also provides the output of the sensing circuit to 62 which is connected to the sensing logic of the tissue stimulator.

The proper operation of the circuit, to reject the common mode properties of the two signals input at 22 and 24, is based on the relationship of resistance means 40, 42, 54 and 58 and the type of signal that is sensed by the sensing systems. The characteristics of the signals are important. The circuit of the invention makes maximum use of these characteristics to attenuate far field artifacts.

In FIG. 2, resistance means 40 is marked as having resistance value R, resistance means 42 has resistance value mR, resistance means 54 has resistance value R' and resistance means 58 has resistance value mR'. To effect proper common mode rejection and to provide an adequate output signal voltage of the circuit at 62 the following relationships of the resistance values are needed:

$R = R'$ $mR = mR'$ mR and mR' are much greater than R and R'

The "m" indicates that the resistance means having resistance value mR and mR' are multiples of the resistance values for R and R'. In operation, as long as there is a signal voltage input to the circuit from the ring or tip electrode to the positive terminal of the first stage amplifier, there will be a signal voltage output from amplifier 36 to the common connection point 46, which supplies a signal voltage to the negative input terminal 50 of second stage operational amplifier 48.

When there is a local depolarization, a signal voltage is sensed by the tip electrode first. The wave front of the advancing depolarization of tissue will then reach the ring electrode. Upon sensing by the tip electrode of the depolarization a signal voltage is applied to point 24 which is connected to the positive input terminal 52 of second stage amplifier 48. Since negative input terminal 50 of amplifier 48 is at zero (because it is grounded through resistors 54, 40 and 42) amplifier 48 produces an output which is fed back through its feedback network to provide a voltage at the negative input terminal 50 which matches the signal voltage the positive input terminal 52.

The negative input terminal is connected to common connection point 56 which is the common connection point for the feedback network of the amplifier and ground 44. This point acts as a voltage divider for the output signal voltage feed back through the feedback network. Since both resistors 42 and 58 have much greater resistance values than resistors 40 and 54, the voltage drop across resistor 58 is small. Therefore, the output by amplifier 48, when only signal voltages are supplied from the tip electrode, is slightly less than double amplitude of the sensed signal voltage. This voltage output is then output from 62 to the tissue stimulator.

During this period, the first stage amplifier positive and negative inputs are connected to ground and each is held to a zero signal voltage. This is accomplished by connecting the positive input for positive terminal 39 to ground through shunt resistor 38 and the negative input terminal 37 to ground directly through resistor 42.

As stated, as the local depolarization wave front advances a signal voltage is sensed by the ring electrode. This signal voltage is applied to point 22 of the circuit. This sensed signal voltage is supplied to positive input terminal 39 of first stage operational amplifier 36. This signal voltage activates the first stage amplifier 36. Since there is a signal voltage at positive terminal 39, the amplifier will attempt to match that voltage at the negative terminal 37 through the feedback network for the first stage. Common connection point 41 acts as a voltage divider. So, the output of amplifier 36 will be at a value great enough to provide a matching signal voltage to negative terminal 37, taking into account the voltage drop across resistor 40.

The signal voltage output by the first stage amplifier 36 is provided to common connection 46. Common connection point 46 besides being a connection point for the feedback network it also connects to the negative input terminal of the second stage amplifier through resistor 54. Common connection point 56 is a connection point between negative input terminal 50, the output from the first stage amplifier 36 and the feedback network. The output from the first stage amplifier 36 experiences a voltage drop across resistor 54 which will result in a voltage substantially the same as that input at 39 of first stage amplifier 36 being applied to the negative input terminal of amplifier 48. Because of the feedback network, the signal voltage output from the first stage will be isolated from the output of the second stage even though they are both connected at 56. The output of the second stage amplifier will then be based on the difference between the signals input at 50 and 52 of second stage amplifier 48. Since the signals at 50 and 52 will be substantially the same, the output of the second stage amplifier 48 will be reduced to a minimal amount. The difference in the inputs will be due, primarily, to the minute internal differences between the components of the circuit. These slight internal differences in the inputs bring about a desirable result, because there will always be an output provided by the second stage amplifier. However, the output will be extremely small compared to the full swing amplitude of the circuit when only one stage is activated alone. The ratio of the outputs in these two situations is in the range of 60:1. Therefore, whenever both amplifier stages are activated there will be a minimal output to the stimulator 10, which generally is not responsive to the minimal output of the sensing circuit.

Since repolarization of depolarized tissue takes place almost simultaneously at both the tip and ring electrode, the circuit output will go to a zero output condition from the minimal output condition at the time of repolarization.

When a far field artifact depolarizes the tissue near the sensing system electrodes, there is virtually simultaneous sensing at tip and ring electrodes due to the characteristics of the wave front. Therefore, the tip electrode supplies a signal voltage to point 24 and the ring electrode supplies a signal voltage to point 22 of the circuit. The characteristics of the far field artifact wave front is that it is broad rather than well-defined or sharp as is found with in the local depolarization wave front. Considering the fact that the both signal voltages are substantially the same and both electrodes sense the signal voltage at substantially the same time, the output of the circuit will be at the minimal output level discussed above. However, this depolarization is essentually attenuated by the circuit. The amplitude of the output of the circuit will exist in the same 60:1 ratio of the full swing amplitude of the circuit.

The significance of this attenuation of the far field artifacts is that the circuit will provide an output signal voltage of an amplitude that will not trigger the tissue stimulator but is detectible to mark the event by a sensing apparatus or section of the tissue stimulator with greater sensing sensitivity. The need for blanking or blocking periods is eliminated because the circuit is only responsive to sensing amplifier circuit output signal voltages generated by local depolarization rather than a far field artifact.

The circuit in FIG. 2 has a diode network 30, which is connected between common connection points 32 and 34. This diode network connects the two inputs at 22 and 24 and has two Schottky diodes in the network. The diode network is generally used as a protection circuit should they be overloading on one of the leads. It will help prevent damage to either stage of the the circuit.

When a unipolar lead system is used, only the tip electrode will supply sensed signal voltages to the sensing amplifier circuit 20. The tip electrode will provide the signal voltage sensed to the input to the circuit at 24. In order to prevent the use of the first stage of the circuit, the first stage is terminated with shunt resistor 38. The shunt resistor 38 is connected to common connection point 32 such that if there is no signal input at 22 both input terminals 37 and 39 of first stage amplifier 36 are grounded to case ground 44. Therefore, the second stage amplifier 48 will act as a single stage differential amplifier. The resistance value of shunt resistor 38 is R″ which is much greater than the resistance value mR of resistor 44. This large resistance value would insure that only in situations when there is no voltage applied to a point 22 that the shunt resistor will be operable within the circuit.

Referring to FIG. 3, the preferred embodiment of the invention is shown generally at 70. The characteristics of the configuration is shown in FIG. 3 is generally as depicted and described in FIG. 2 with several modifications for allowing operation of the circuit with either a unipolar or bipolar lead system. Further, the circuit, when a bipolar lead system is used, can be configured to provide a signal voltage output indicative of a unipolar or bipolar lead system as desired by the operator without any significant changes to the circuit.

Although, from the foregoing, it is evident that the sensing circuit of the present invention can be connected to either a unipolar or bipolar lead system. The following description will be generally pertaining on the use of a bipolar lead system since this configuration attenuates far field artifacts. FIG. 2 shows resistors 26 and 28; and protection diode network 30. FIG. 3 does not specifically show 26, 28 and 30. These are present but not specifically set forth in FIG. 3, because 26 and 28 represent input impedence for each input, and protection diode network 30 can be replaced by any component that would prevent damage to the amplifiers of the circuit.

Referring to FIG. 3, tissue stimulator 72 is connected to the bipolar lead systems 80 and 82 at 76 and 78, respectively. These lead systems acts as a conduit for electrical pulses output from the stimulator to the tissue to be stimulated and for sensing depolarization signal voltages in the adjacent tissue. The tissue stimulator has a sensing logic and control section 74 disposed therein for interpreting the amplified signal voltage sensed by the lead system. This section will determine whether the depolarization event was a sensed R-wave, P-wave pulse, atrial or ventricular pulse. This sensing logic and control section has inputs to the operating logic of the stimulator and helps determine the proper pacing scheme for the tissue stimulator.

As stated, bipolar lead 80 is connected to the output position 76 of the stimulator. Although, it is described as being a bipolar lead, it is clear from the foregoing paragraphs that it could be a unipolar lead.

The bipolar leads 80 and 82 are shown as one line. However, in actuality, leads 80 and 82 consist of a twisted pair of electrode wires. One line is connected to tip electrode 84 and the second line is connected to ring electrode 86. This latter line is commonly referred to as the return line. Therefore, when the lead is used for pacing, the negative electrode (or tip) 84 outputs a negative voltage for stimulation of the cardiac tissue and the circuit is completed by an electrode 86 returning the voltage back to the case ground of the tissue stimulator 72. The negative output pulse travels from the tip electrode 84 through the body fluids to the ring electrode 86 and back to case ground of tissue stimulator 72. This general return line is shown as 79.

Although, the previous description was for the atrial lead system attached to V out, 76, the same description is applicable to ventricular lead system 82 which is attached to stimulator. This bipolar system is connected to V out for the ventricular pulse at 78 of tissue stimulator 72. For the remainder of the description of the circuit of the invention, any reference to either the atrial and ventricular sensing circuits will be applicable to both because they are identical in configuration and operation.

When bipolar leads 80 and 82 are used for sensing rather than pacing, the tip electrodes 84 and 126, and ring electrodes 86 and 128 are all used for sensing signal voltages indicative of depolarization of the cardiac tissues in the atrium and ventricle.

When there is a local depolarization of the cardiac tissue near the tip and ring electrodes, the depolarization wave front will travel through the cardiac tissue reaching the tip electrode first and then the ring electrode. The time of travel is brief because the distance between the tip and ring electrode is small. Because there is a well defined wave front, the depolarization will be first sensed by the tip electrode, which is directly adjacent to the cardiac tissue, and then sensed by the ring electrode which is spaced away from the tip electrode. This will cause a signal voltage differential or phase difference between the two amplifier stages based on the time it takes for the wave front to travel the distance between the tip electrode 84 or 126 and ring electrode 86 or 128, respectively. This differential is noted by the sensing amplifiers. The output of the sensing circuit will be indicative of this phase difference in detected signal voltages. The relationship of output of the circuit is:

$$e \cong (M+1)(e_2 - e_1)$$

where,
output e = signal voltage output by the circuit;
M = the resistance multiple for the resistor pairs;
$e_1$ = the input signal voltage in the first stage; and
$e_2$ = The input voltage to the second stage.

When there is a far field artifact that cause depolarization of the tissue or near the distal end of the lead system, both stages are simultaneously activated because of the broad nature of the wave front. Because of this there is attenuation of the signal voltages sensed by the electrodes. This attenuation by the circuit of the invention prevents false triggering of the tissue stimulator. Therefore, these sensed signal voltages are attenuated to an extent that will prevent the appearance of a locally generated depolarization event when it is a far field artifact.

Viewing the bipolar lead systems 80 and 82 in their sensing configuration, when there is a locally generated depolarization of tissues in the atrium or ventricle, it will be sensed by tip electrode 84 or 126 first and signal voltage is supplied to connection point 114 and 160 in the respective leads. That signal voltage will be amplified by second stage amplifiers 96 or 142. The respective circuits provide a voltage output from the second stage amplifiers 96 or 142 to connection points 118 and 164.

As a wave front reaches ring electrode 86 or 128, the sensed signal voltage is applied to switch connection 90 of switch 88 or switch connection 132 of switch 130. The switches 88 and 130 are used to allow or disallow signal voltages sensed at the ring electrodes 86 or 128 to be input to the first stage amplifiers 94 or 136. This switch allows a bipolar lead system to sense as a unipolar sensing system if desired.

Considering that both switches 88 and 130 are closed, so that there is utilization of both the stages of the circuit, the signal voltages detected by ring electrodes 86 and 128 are input to positive input terminal 98 of amplifier 98 and positive input terminal 138 of amplifier 136. In situations when switch 88 or 130 is open, both input terminals 98 and 100 of operational amplifier 94 and inputs 138 and 140 of operational amplifier 136 are connected through shunt resistors 102 and 148 to case ground 103, thus, terminating the first stage to ground.

Returning to the situation when switches 88 and 130 are closed, signal voltages sensed by ring electrodes 86 or 128 are supplied to positive input terminal 98 of operational amplifier 94 or positive input terminal 138 of operational amplifier 136. When these signal voltages are applied to the positive input terminals of the respective operational amplifiers 94 or 136, there is an output from the first stage amplifiers to common connection point 108 or 156. The negative input terminal of operational amplifiers 94 and 136 are connected to a case ground 103 through resistance means 104 and 152. The output signal voltages from operational amplifiers 94 or 136 are applied to the respective feedback networks of the operational amplifiers. The respective feedback networks of the first stage amplifier, have resistors 110 and 158. The feedback networks supply the matching signal voltages to the negative input terminals of the respective operational amplifiers, because of the ground connection. The voltage drop across the feedback network is dependant on the resistor pairs 104 and 110, or 156 and 158.

The respective output signal voltages of first stage operational amplifiers 94 and 136 are supplied to the negative input terminals of second stage operational amplifiers 96 and 142 through resistors 112 and 159, respectively. The application of the first stage amplifier output to the negative input terminals 99 of operational amplifier 96 and negative input terminal 146 of operational amplifier 142 provides the matching signal voltage to that input of the respective positive input terminals. There no longer exists a difference in voltages at amplifiers 96 and 142 inputs, as seen by the second stage amplifiers. The output of the second stage will become minimal compared to the full-swing amplitude once both stages are activated. The output from the second stage, though minimal, is supplied to common connection point 118 and 164, respectively. The output signal voltages supplied to the respective feedback networks of the two second stage amplifiers serve only to isolate the input voltages and will only increase negatively if an imbalance is seen at the inputs to either second stage amplifier. Therefore, the feedback networks have the same responsibilities as previously discussed for FIG. 2.

The amplified signal voltages, whether at a full-swing amplitude or minimal amplitude, are supplied to points 122 and 168 of respective circuits. These points are connected to the sensing logic and control section 74 of tissue stimulator 72. The respective inputs at 170 and 124 either meet or do not meet the threshold limitations of section 74 of stimulator 72 which determines the pulsing scheme of tissue stimulator.

When there is a far field artifact detected at the respective tip and ring electrode of the atrial and ventricular lead systems, there is simultaneous input of the signals into the respective stages of the full differential amplifiers of the circuits of the invention. As previously described, because of the internal differences of the circuit components, there will always be an output voltage from the sensing circuit of the invention. Because of this slight voltage difference there will be a minimal output compared to the normal output caused by a local depolarization of tissue. Therefore, the far field artifacts could be seen on an oscilliscope, and such far field effects would be totally attenuated as viewed by the stimulator and would not effect the pacing scheme of it.

The tissue stimulator would not respond actively to any event which was not local in nature. Tissue stimulator 72 would sense continuously without the need of imposing blanking or blocking periods to nullify any far field artifacts sensed by the sensing system.

The terms and expressions which are employed here are used as terms of description and not of limitation. And there is no intention, in the use of such terms and expressions, of excluding equivalence of the feature shown, and described, or portions thereof, it being recognized that various modifications are possible in the scope of the invention as claimed.

I claim:

1. A sensing amplifier circuit for a tissue stimulator for supplying or attenuating far field signal voltage artifacts comprising:
   (a) a first amplifier means having a first input terminal connected to a switch means connected to a second signal voltage output of a sensing means, a second input terminal connected to ground with a first resistance means disposed between said second input terminal and ground, and said first amplifier means provides a first amplifier signal voltage output;
   (b) a first feedback network having a second resistance means therein disposed connected between said first amplifier signal voltage output and said second input terminal of said first amplifier;
   (c) a third resistance means connected between said first input terminal and ground;
   (d) a second amplifier means having a first input terminal connected to a first signal voltage output from said sensing means, a second input terminal connected to said first amplifier signal voltage output with a fourth resistance means disposed between said first amplifier signal voltage output and said second input terminal, and said second amplifier means provides a second amplifier signal voltage output for input into a sensing circuit of said tissue stimulator; and
   (e) a second feedback network having a fifth resistance means therein disposed connected between said second amplifier signal voltage output and said second input terminal of said second amplifier.

2. The circuit as recited in claim 1 wherein said first and second amplifier means include operational amplifiers.

3. The circuit as recited in claim 1 wherein said first and fifth resistance means are equal in resistance value.

4. The circuit as recited in claim 1 wherein said second and fourth resistance means are equal in resistance value.

5. The circuit as recited in claim 1 wherein the third resistance means have a larger resistance value than said first, second, fourth or fifth resistance means.

6. A sensing amplifier circuit for a tissue stimulator for supplying or attenuating far field signal voltage artifacts detected in tissue by sensing means, such sensing means having a first and a second output and the tissue stimulator having a case establishing a case potential, the circuit comprising:
   a first amplifier having an input adapted for connection to the sensing means first output, the first amplifier including means for providing at an output thereof a voltage substantially the same as the voltage applied at the input thereof and resistive means for holding the amplifier input at case potential when no input signal is applied to such input; and
   a differential amplifier having a first input connected to the output of the first amplifier and a second input adapted for connection to the sensing means second output, the output of the differential amplifier adapted for connection to the tissue stimulator.

7. The circuit as recited in claim 6 wherein the sensing means comprises bipolar sensing means including a tip electrode and a ring electrode and the first amplifier is adapted for connection to the ring electrode and the second input of the differential amplifier is adapted for connection to the tip electrode.

8. The circuit as recited in claim 7 wherein the circuit includes switching means connected to the first amplifier input and adapted for connection to the ring electrode, the switching means being for connecting the ring electrode to or disconnecting the ring electrode from the first amplifier input.

9. A sensing amplifier circuit for a tissue stimulator for supplying or attenuating far field signal voltage artifacts detected in tissue by sensing means, such sensing means including a tip electrode and a ring electrode, and the tissue stimulator having a case establishing a case potential, the circuit comprising:
   a first amplifier having an input, means for providing at an output thereof a voltage substantially the same as the voltage applied at the input thereof, and holding means for holding the amplifier input at case potential when no input signal is applied to such input;
   switching means connected to the first amplifier input and adapted for connection to the ring electrode, the switching means being for connecting the ring electrode to or disconnecting the ring electrode from the first amplifier input; and
   a differential amplifier having a first input connected to the output of the first amplifier and a second input adapted for connection to the tip electrode, the output of the differential amplifier adapted for connection to the tissue stimulator.

* * * * *